United States Patent [19]

Bischoff et al.

[11] Patent Number: 5,275,955
[45] Date of Patent: Jan. 4, 1994

[54] PROCEDURE FOR ESTABLISHING THE PRESENCE OF LIVE HOUSE-DUST MITES

[75] Inventors: Edelbert Bischoff, Kirchheim-Bolanden; Gert Wetter, Worrstadt, both of Fed. Rep. of Germany

[73] Assignee: Gesellschaft fur Hausbiologische Forschung mbH, Fed. Rep. of Germany

[21] Appl. No.: 520,137

[22] Filed: May 4, 1990

Related U.S. Application Data

[63] Continuation of Ser. No. 217,127, Jul. 6, 1988, abandoned, which is a continuation of Ser. No. 887,284, Jul. 21, 1986, abandoned.

[30] Foreign Application Priority Data

Jul. 19, 1985 [DE] Fed. Rep. of Germany ....... 3525883

[51] Int. Cl.$^5$ ............................................. G01N 33/36
[52] U.S. Cl. .......................................... 436/86; 436/10; 436/63; 436/164; 436/169; 436/183; 436/903
[58] Field of Search ................... 436/10, 63, 164, 169, 436/183, 903

[56] References Cited

U.S. PATENT DOCUMENTS

| | | | |
|---|---|---|---|
| 3,585,004 | 6/1971 | Mast | 422/56 |
| 3,684,451 | 8/1972 | Linoli et al. | 436/169 X |
| 3,862,327 | 1/1975 | Covey et al. | 514/517 |
| 3,904,760 | 9/1975 | Ariyan et al. | 514/444 |
| 3,983,244 | 9/1976 | Ariyan et al. | 514/444 |
| 4,003,940 | 1/1977 | Covey et al. | 558/60 |
| 4,104,401 | 8/1978 | Covey et al. | 514/517 |

OTHER PUBLICATIONS

Allergy and Immunology, vol. 24, pp. 18-28 Bronswijk et al. (1978).
R. Voorhorst et al, Allergologie 2 (1978), 93 to 101.

*Primary Examiner*—Lyle A. Alexander
*Assistant Examiner*—Harold Pyon
*Attorney, Agent, or Firm*—Ladas & Parry

[57] ABSTRACT

A procedure for establishing the presence of live housedust mites in a textile sheet-like article, in which the housedust mites are allowed to migrate onto the surface of the article to be tested or are caused to start such a migration, if appropriate by the action of heat, the housedust mites which have migrated being picked up at this point and subsequently identified.

20 Claims, No Drawings

PROCEDURE FOR ESTABLISHING THE PRESENCE OF LIVE HOUSE-DUST MITES

This is a continuation of copending application Ser. No. 07/217,127 filed on Jul. 6, 1988 which is a continuation application of application Ser. No.: 06/887,284 filed on Jul. 21, 1986, both now abandoned.

In numerous countries, small pests such as housedust mites represent an increasing nuisance which affects, in particular, persons suffering from allergies. Housedust mites multiply very prolifically in suitable biotopes and, during their lifespan, produce an amount of allergen containing excrement which exceeds their body weight by a factor of many thousands. Housedust then contains excrement, dead and live mites and is found, in particular, in textile structure in houses, such as mattresses, upholstery and carpets and is raised as very fine dust when using, or walking on, the textile articles. Housedust allergies can develop into potentially fatal complaints.

If the intention is to eliminate housedust mites as a source of further allergen-containing dust, the following questions have to be answered: where do the mites reside? What number of live mites are present? What species of mites are found in what development stages? Has the use of mechanical means, such as vacuum cleaning or beating, been effective? Has it been possible to reduce or eliminate the mite population by using an acaricide? Has the agent a permanent effect? Could new mites develop from the eggs which are still present? After what period of time is there a renewed infestation with housedust mites, etc.

At present these questions can only be answered by examining the dust collected by vacuum cleaning for the presence of mites. The best proven procedure for this purpose is the flotation method. In this method, the dust is transferred into a suitable liquid medium on the surface of which dead and live mites float. The sites are transferred from the medium onto a slide by means of a dissecting needle and are subsequently identified under the microscope. Long experience is necessary to distinguish between dead and live mites. A distinction can be made on the basis of the finding that live mites are as a rule free of damage. By contrast, dead mites or mites which were already dead before the dust sample was collected have always lost some limbs, masticatory organs or spines. Live mites are considered to be those which are still recognisably alive or undamaged and round and firm. This is because some mites do not survive the identification procedures.

However, the main disadvantage of this method is not problems with identifying live mites. On the contrary, it is due to the procedure. In a dust sample in fact only the housedust mites which have entered the dust sample during vacuum cleaning can be detected. There is no indication, however, as to what proportion of dust or mites can actually be detected by vacuum cleaning of a textile structure.

Recent investigations have shown that vacuum cleaning eg. a carpet once or twice results in only a limited proportion of the dust present, including dead and live mites, being collected.

Moreover, examining a dust sample can seldom provide information about the entire sheet-like structure, for example, carpet, from which the sample was taken. It is not possible by this means to obtain information as to where the mites, in particular live mites, do actually reside.

The object of the invention is therefore to develop a procedure by means of which reliable and rapid information on the presence and estimated population of live housedust mites can be obtained under laboratory and practical conditions. Another object is to obtain information on the distribution of the mites over the sheet-like element examined and to provide, in a simple manner, the possibility of evaluating the live mites under the microscope as regards their species, their sex and their development stage. This object has been achieved by means of the procedure according to the invention.

The procedure takes account of the ecological conditions of a mite biotope and of the mobility of mites. Although housedust mites can endure ecological conditions which are unfavorable for them, eg. relatively low temperatures, over a prolonged period and their eggs in particular are relatively insensitive to climatic fluctuations, populations which are to develop require a microclimate of about 25° C. and 65–85% relative atmospheric humidity.

If, then, these conditions are changed the mites attempt to reach a sheet-like element which offers more favorable living conditions. For example they avoid elevated temperature (heat) and the associated change in the relative atmospheric humidity. In a preferred embodiment of the procedure according to the invention this fact is utilized to bring about a forced directed migration.

In a simpler embodiment of the procedure according to the invention for cases in which exposure to heat has to be dispensed with, use is made merely of the natural mobility of the mites.

The present invention therefore relates to a procedure for establishing the presence and distribution of live housedust mites.

The statements below are intended as a detailed description and explanation of this procedure according to the invention.

The article to be tested for infestation with mites is a textile sheet-like article, that is, a textile article having exposed surfaces. Textile sheet-like structures of this type which may be mentioned are for example carpets, upholstery, mattresses, beds, textile wallcoverings etc.

An essentially continuous collecting surface, such as an adhesive film, is used.

Suitable films with an adhesive coating are the customary products. Particularly preferred adhesive films are those in which the adhesive takes up (adhesively) the mites but is not transferred to the article to be tested.

In order to improve the contact of the adhesive film with the front or surface of the textile article, it is preferred to weight the film in turn with a suitable plate-shaped object (such as, for example, a glass sheet). Because of the sensitivity of housedust mites to light it is furthermore preferred to carry out the weighting by means of a darkened or opaque plate or by means of a glass sheet which is coated (for example with an opaque film or sheet).

To facilitate handling of the adhesive film laden with mites, the adhesive side of the film is preferably coated with a transparent non-adhesive protective film. Protective films of this type which can be used are the customary plastic sheets (such as for example polyethylene sheets).

In a further preferred embodiment the adhesive layer of adhesive film can additionally contain substances which attract or stain the mites to be assessed. Examples of lures of this type are pheromones or the like. An example of staining is combined extraction and formation of an azo dyestuff with the excrement constituent guanine, as described in assignee's Ser. No. 016,623 filed Feb. 19, 1987; the protective film can also contain an azo coupling component or extractant of this type.

In the simplest embodiment of the procedure according to the invention the mites are taken up on the front or surface of the article, that is without making use of a heat source, due to their natural mobility (migration). This method is particularly suitable for articles which cannot be subjected to the action of heat (from their rear). Even in this case the procedure according to the invention provides information about the presence of live mites. In this case quantitative evaluations can moreover also be carried out as shown in the statements below (compare II).

In another embodiment the procedure according to the invention is preferably carried out in a manner such that the rear side of the article to be tested is subjected to the action of heat and the mites are caused to migrate more frequently onto the front or surface. In this embodiment the exposure to heat is preferably carried out by means of a flat heat source. This can, for example, be a heatable surface (hot plate) made of metal, or if appropriate of ceramics, glass or a suitable plastic. The flat heat source can moreover also be used in the form of a heating pad which may be modified if appropriate. This embodiment of the procedure according to the invention (with the action of heat) is likewise explained below (under I).

However, it is also possible to combine the two embodiments mentioned above (namely II, due to the natural mobility; and I, due to the action of heat). The results of such an operation are explained below (under III).

I. METHOD WITH THE ACTION OF HEAT ("HEAT ESCAPE METHOD")

A textile sheet-like structure to be tested (for housedust mites) is placed on a so-called hot plate. The latter is preferably a metal surface which is capable of being heated uniformly in any form. An example which may be mentioned is an aluminum block of size 120×30 cm and thickness 3 cm. A copper pipe with parallel windings which are embedded in crystalline quartz sand is located inside the block. The pipe is connected to a thermostat which conducts heat transfer oil of the desired temperature through the system.

When a piece of carpet is laid with its back onto such a hot plate, the heat transfer oil is heated, after switching on the heater, from room temperature to 150° C. After about 60 minutes the carpet pile reaches a temperature of about 70° C.

During this given time (60 minutes) the mites successively leave their biotopes in the depths of the carpet pile and migrate in the direction of the carpet surface.

At the start of the experiment an adhesive film is placed onto the carpet surface, which film takes up the mites as they arrive and the consistency of the adhesive layer of which is preferably chosen so that the carpet is not soiled with adhesive. In order to obtain uniform contact between adhesive film and carpet surface, the adhesive film is preferably in turn weighted with a suitable plate (eg. glass sheet). In order to take account of the sensitivity of housedust mites to light a dark plate is preferably used or the glass sheet is covered with a dark or opaque film or sheet.

The adhesive film is then peeled off the carpet pile and, to fix the result, a polyethylene film protective sheet is preferably applied to its adhesive side. This structure can be used to count, identify and locate the housedust mites and thus obtain information on the identity, number and distribution of the mites in the carpet. It is also possible to add to the cover film a reactant for a mite detection procedure, for example a staining reaction, for example an azo coupling component or an extractant if formation of an azo dyestuff is intended.

A second adhesive film can immediately be placed onto the piece of carpet under examination in the manner described and this second film remains there for a further hour under the same conditions. The temperature in the depth of the pile is increased to about 100° C. during this procedure. It is detected in this way whether still more mites are reaching the adhesive film. As a rule, however, only a few percent of the number of mites originally found is obtained thereby.

(A commercial product produced by Beiersdorf under the name "Tesa Schutzfolie 5609 [Tesa protective film 5609]" has proved suitable as an adhesive film.)

If counted mites are released on textile surfaces and are allowed to hide for a certain period of time, when carrying out the procedure according to the invention the preponderance (about ⅔) of the mites released is found on the adhesive film (Example A). As a rule, they are still recognisably alive there and can be identified under the microscope as regards mite species, sex and development stage.

By means of this procedure it is however also possible to examine carpets and other textile sheet-like structures with natural infestation with mites and to assess them largely quantitatively. The same applies to pieces of carpet and other textiles which have been taken as samples from households of persons suffering from an allergy.

The procedure can furthermore be carried out on the spot, that is to say in the households of persons suffering from an allergy, by pushing a mobile sheet-like heat source, eg. in the form of a heating pad which may be modified if necessary, under the carpets which are not adhered to the entire surface they cover. Upholstery can be examined in a corresponding manner, preferably when the latter can be opened—as is frequently the case with more recent furniture—by means of a zip fastener or when their seams can be easily undone.

In the case of articles where it is not possible to bring about directed action of heat, an adhesive film which is preferably covered—as described—can be applied to obtain a first indication as to whether live mites are present. This method too can be used to carry out largely quantitative determination albeit so as to estimate the number of mites present with reduced reliability (see section II).

EXAMPLE A

Recovery of Small Pests Released

To evaluate the "Heat Escape Method" its validity and yield, pieces of carpet (type nylon/velour/raw undyed material) of size 0.25 m² are divided into three parts of the same size. Between 40 and 200 mites are released on each of these parts. After a period of 2 hours in which they could hide an adhesive film placed onto the pieces of carpet, covered with a plate and the exposure to heat is started as described above under I. The result is finally analyzed after 1 and 2 hours likewise as described above.

Results (Example according to experiment 3 in Table 1):

1st third: 75 mites released, 51 mites recovered on film
2nd third; 171 mites released, 101 mites recovered on film
3rd third: 122 mites released, 82 mites recovered on film.

Summary:
368 mites released, 234 mites recovered on film
Proportion of mites recovered: 64%.

Repetition of this test (compare Nos. 1, 2, 4 and 5 with 3 part-pieces in each case in Table 1) leads to results with the number of mites recovered of the same order of magnitude.

The proportion of mites recovered is on average 65%±5% (for this reason a factor of 100:65 is used below. This proportion of mites recovered is substantial. This substantial proportion of recovery together with the relatively small statistical deviation makes this ascertainment significant for the purpose of estimating the total number of live mites in the portion of the article to which the heat is applied.

For details see Table 1.

EXAMPLE B

"Heat Escape Method" in the Case of Pieces of Carpet Naturally Infested

After determining the recovery factor or previously determined ratio of mites picked up in a defined area in a preliminary test according to Example A it is possible to determine the population density of carpets with natural infestation by means of the "Heat Escape Method" and to obtain a picture of the distribution over the sheet-like element concerned.

Given favorable climatic and feeding conditions the populations multiply within a few months from 1000 to 10,000 to 50,000 mites per 0.25 m².

Details can be found in Table 2 of the estimated number of mites on the basis of the "heat escape method" utilizing the recovery factor determined under Example A (and Table 1).

By means of the procedure according to the invention it is possible to make statements on the population density of mites in textile sheet-like structures which may occur in a density of up to 200,000 mites per m²; in extreme cases as many as 500,000 mites per m² have been observed.

II. METHOD WITHOUT ACTION OF HEAT DUE TO NATURAL MOBILITY ("MOBILITY TEST") UNDER USUAL CLIMATIC CONDITIONS OF TEMPERATURE AND HUMIDITY

In this method an adhesive film is placed onto the textile surface to be examined, for example carpet, mattress or upholstery, is preferably covered, removed after a given residence time of up to 24 hours (preferably with a protective film applied) and subsequently evaluated.

After placing a counted number of mites onto the surface for test purposes and after a period of 2 hours to permit the mites to hide so as to approximate their usual location in the object to be tested, about 30% of the mites employed are recovered on the film after an application time of 24 hours under climatic conditions which are favorable for the mite biotope (25° C., 75% relative atmospheric humidity). Details can be found in Table 3.

If the test conditions are less favorable for the assessment of the mite mobility, for example room temperature but only low atmospheric humidity (25% relative atmospheric humidity), about 8% of live mites are still found (see Table 4).

Both cases are possible in practice. The number of mites recovered by the procedure according to the invention utilizing the intrinsic mobility of small pests is therefore between about 8% and about 30% depending on the particular climatic conditions which prevail in practice. This percentage recovery over the given period of time involved (up to 24 hours) is significant for determining the total number of live mites in the portion of the article to which the collecting surface is applied.

Reference is made to the above statements under I as to further details of this method, for example the evaluation of the films.

III. COMBINED USE OF THE TWO METHODS MENTIONED ABOVE (MOBILITY AT ROOM TEMPERATURE "MOBILITY TEST", AND DIRECTED MOVEMENT UNDER THE ACTION OF HEAT, "HEAT ESCAPE METHOD") IN ORDER TO DETERMINE THE RECOVERY FACTOR FOR THE MOBILITY TEST UNDER KNOWN CONDITIONS OF TEMPERATURE AND HUMIDITY.

In this way an approximate evaluation of the mites recovered in the Mobility Test with natural infestation of textile sheet-like structures is possible. The combined method has therefore also already been used in the test described in Table 4.

When the two methods are combined, the intrinsic mobility of the mites under favorable climatic conditions initially results in a mite recovery rate of about 30%. This corresponds to the values already found in Table 3.

The population which remains is then subjected to the action of heat as described under I. The number of mites found in this case on the adhesive film is extrapolated by the previously determined ratio of 100:65 as likewise described under I. The sum of the value thus obtained by the "Heat Escape Method" and that obtained by the Mobility Test is the total population and hence makes possible evaluation of the number of mites determined by the Mobility Test as a percentage of this total population. Details can be found in Table 5.

Reference is made to the above statements under I and II for further details.

As mentioned above in connection with No. I the procedure according to the invention in its embodiment as "Heat Escape Method" can be used to drive out the majority of live housedust mites present in the infested article and this majority of mites can then be picked up (eg. by means of an adhesive film). The present application therefore also relates to the use of the procedure according to the invention for controlling (removing) live housedust mites wherein the rear side of the article to be treated (for infestation with live mites) is subjected to the action of heat, the mites are thereby caused to migrate primarily onto the front or surface and the mites which have migrated are then picked up and, if appropriate, identified. Here again the exposure to heat is preferably carried out by means of a flat heat source.

In respect of further details of a control procedure of this type reference is made to the above statements made in connection with the "Heat Escape Method" the content of which is likewise of relevance here (compare the corresponding statements made under I, it of course being possible to carry out a heat treatment in one stage instead of the two-stage heat treatment).

The new control procedure can be carried out with both subsequent identification of the mites (as explained above) and without such an identification; in the latter case the mites which have been picked up, eg. by means of a laden adhesive film, are then simply thrown away together with the film.

TABLE 1

Result of the "Heat Escape Method", on a carpet surface of 0.25 m² in each case in the preliminary test
(A: Mites released, B: mites recovered)

| | Experiment No. | | | | | | | | |
|---|---|---|---|---|---|---|---|---|---|
| | 1 | | 2 | | 3 | | 4 | | 5 |
| | A | B | A | B | A | B | A | B | A | B |
| Part piece a | 104 | 72 | 57 | 44 | 75 | 51 | 72 | 45 | 115 | 90 |
| Part piece b | 156 | 102 | 178 | 108 | 171 | 101 | 128 | 83 | 174 | 126 |
| Part piece c | 47 | 34 | 110 | 58 | 122 | 82 | 161 | 94 | 47 | 20 |
| | 307 | 208 | 345 | 210 | 368 | 234 | 361 | 222 | 336 | 236 |
| Proportion of mites recovered | 68% | | 61% | | 64% | | 61% | | 70% | |

TABLE 2

Number of mites recovered in the "Heat Escape Method" (temperature change from room temperature to about 100° C.): (from pieces of carpet of size 0.25 m² naturally infested)

| | Experiment 1 | Experiment 2 |
|---|---|---|
| Original number of mites | 1000 | 1000 |
| Development time in months | 4 | 4 |
| Determination of mites by the "Heat Escape Method" | | |
| Total number of mites found | 31,050 | 11,930 |
| Total number of mites present (extrapolation by a factor of 100:65) | 47,770 | 18,350 |

TABLE 3

Result of the Mobility Test on a carpet surface of 0.25 m² in the preliminary test
(A: mites released, B: mites recovered)
(25° C., 75% relative atmospheric humidity)

| | Experiment No. | | | |
|---|---|---|---|---|
| | 1 | | 2 | |
| | A | B | A | B |
| Part piece a | 70 | 25 | 239 | 69 |
| Part piece b | 140 | 45 | 180 | 67 |
| Part piece c | 269 | 69 | 110 | 34 |
| | 479 | 139 | 529 | 170 |
| Proportion of mites recovered at high relative atmospheric humidity | 29% | | 32% | |

TABLE 4

Number of mites recovered in the Mobility Test at low relative atmospheric humidity (23° C., 25% relative atmospheric humidity) (from pieces of carpet of size 0.12 m² naturally infested)

| | Experiment No. | | | |
|---|---|---|---|---|
| | 1 Number of mites | 2 Number of mites | 3 Number of mites | 4 Number of mites |
| 1. Mobility Test | 971 | 1,125 | 1,548 | 901 |
| 2. Determination of mites which remained according to the "Heat Escape Method" and extrapolation by a factor of 100:65 | 11,145 | 13,255 | 14,271 | 12,954 |
| Total population | 12,116 | 14,380 | 15,819 | 13,855 |
| Number of mites recovered in the Mobility Test at low relative atmospheric humidity | 8.0% | 7.8% | 9.8% | 6.5% |

TABLE 5

Number of mites recovered in the Mobility Test at favorable relative atmospheric humidity (25° C., 75% relative atmospheric humidity) and subsequent "Heat Escape Method" (from a naturally infested carpet of size 0.25 m² and examination of individual part pieces of size approx. 0.04 m²)

| | Experiment No. | | | |
|---|---|---|---|---|
| | 1 Number of mites | 2 Number of mites | 3 Number of mites | 4 Number of mites |
| 1. Mobility Test | 3,800 | 3,200 | 3,200 | 2,400 |
| 2. Subsequent "Heat Escape Method" (direct determination) | 5,650 | 6,000 | 5,000 | 2,650 |
| 3. Extrapolation of the values obtained according to 2. by a factor of 100:65 | 8,690 | 9,230 | 7,690 | 4,080 |
| Total population (1 + 3) | 12,490 | 12,430 | 10,890 | 6,480 |
| Number of mites recovered in the Mobility Test at high relative atmospheric humidity | 30% | 26% | 29% | 37% |

We claim:

1. A process for estimating the number of live house dust mites which are present in a textile article having exposed surfaces, wherein:
   (1) (a) the mites are allowed to migrate over a given period of time under conditions consisting essentially of temperature and humidity affecting the migration of mites onto a surface of a textile article to be tested,
   (b) an essentially continuous adhesive collecting surface to which the mites adhere and which has a defined area is maintained in contact with said surface of the article over said period of time, the mites which have migrated being picked up by said collecting surface including said defined area, and (c) said collecting surface is subsequently examined to determine the number of mites collected within said defined area, (d) said given period of time being sufficient under said conditions to cause a significant percentage of the mites present within a portion of the article adjacent the surface of the article to which the collecting surface is applied to migrate to said surface of said article and be picked up by said collecting surface, and (2) the total number of mites within said portion of the article is then estimated on the basis of (a) said determined number of mites within the defined area and (b) a recovery factor determined by allowing counted live mites to hide in a textile article and counting the mites recovered.

2. A process according to claim 1, wherein the mites are allowed to migrate over said period of time under normal ambient conditions of use existing in said area of the textile article, said conditions affecting the migration of mites including the temperature and humidity of the atmosphere in contact with the textile article.

3. A process according to claim 2, in which the given period of time is up to about 24 hours.

4. A process according to claim 1, in which the distribution of said mites in said defined area of the collecting surface is also ascertained.

5. A process according to claim 1, in which the given period of time is within the range of about 1 hour to about 24 hours.

6. A process according to claim 1, in which the identity and distribution of said mites in said defined area of the collecting surface are also ascertained.

7. A process according to claim 1, wherein said estimation of the total number of mites within said portion of said article is carried out by dividing (a) said determined number of mites within the defined area by the (b) recovery factor, said recovery factor being obtained by dividing the number of mites recovered within a defined area by the number of mites allowed to hide in said article.

8. A process according to claim 1, wherein a rear surface of the article to be tested is subjected to the action of heat, said heat being sufficient over said period of time to cause a substantial portion of the live house dust mites within a portion of the article adjacent the rear surface to which the heat is supplied to migrate primarily to a front surface of the article, said front surface being in contact with the collecting surface.

9. A process as claimed in claim 8, wherein the action of heat is provided by means of a flat heat element.

10. A process according to claim 8, wherein the article to be tested is a carpet.

11. A process according to claim 8, wherein said estimation of the total number of mites within said portion of said article is carried out by dividing (a) said determined number of mites within the defined area by the (b) recovery factor, said recovery factor being obtained by dividing the number of mites recovered within a defined area by the number of mites allowed to hide in said article.

12. A process according to claim 8, in which the collecting surface comprises an adhesive coating on a film.

13. A process according to claim 11, in which the collecting surface comprises an adhesive coating on a film.

14. A process as claimed in claim 13, wherein the film with the adhesive coating is weighted with a darkened or opaque plate.

15. A process as claimed in claim 13, wherein a transparent non-adhesive protective film is applied to the adhesive coating which has picked up the mites to facilitate counting and microscopic examination of the mites.

16. A process as claimed in claim 13, wherein the adhesive coating contains substances which furthermore attract the mites.

17. A process as claimed in claim 13, wherein the adhesive coating contains substances which facilitate identification of the mites.

18. A process as claimed in claim 17, wherein the adhesive coating contains a substance which develops a dyestuff in conjunction with a part of the mite's body.

19. A process for estimating the number of live house dust mites which are present in a textile article having exposed surfaces, wherein:

(1) (a) the mites are allowed to migrate over a given period of time under conditions consisting essentially of temperature and humidity affecting the migration of mites onto a surface of a textile article to be tested, (b) an essentially continuous adhesive collecting surface to which the mites adhere and which has a defined area is maintained in contact with said surface of the article over said period of time, the mites which have migrated being picked up by said collecting surface including said defined area, and (c) said collecting surface is subsequently examined to determine the number of mites collected within said defined area, (d) said given period of time being sufficient under said conditions to cause a significant percentage of the mites present within a portion of the article adjacent the surface of the article to which the collecting surface is applied to migrate to said surface of said article and be picked up by said collecting surface, and (2) the total number of mites within said portion of the article is then estimated on the basis of said determined number of mites within the defined area.

20. A process according to claim 19, wherein a rear surface of the article to be tested is subjected to the action of heat, said heat being sufficient over said period of time to cause a substantial portion of live house dust mites within a portion of the article adjacent the rear surface to which the heat is supplied to migrate primarily to a front surface of the article, said front surface being in contact with the collecting surface.

* * * * *